(12) United States Patent
Vaisnys et al.

(10) Patent No.: US 8,185,196 B2
(45) Date of Patent: May 22, 2012

(54) PCB BLADE CONNECTOR SYSTEM AND METHOD

(75) Inventors: Gintaras A. Vaisnys, Guilford, CT (US); Giovanni C. Meier, Guilford, CT (US); Glenn W. Laub, Guilford, CT (US); Benny Chi, Guilford, CT (US)

(73) Assignee: Defibtech, LLC, Guilford, CT (US)

( * ) Notice: Subject to any disclaimer, the term of this patent is extended or adjusted under 35 U.S.C. 154(b) by 659 days.

(21) Appl. No.: 12/383,314

(22) Filed: Mar. 23, 2009

(65) Prior Publication Data

US 2009/0187225 A1 Jul. 23, 2009

Related U.S. Application Data

(62) Division of application No. 11/386,051, filed on Mar. 21, 2006, now Pat. No. 7,912,543.

(51) Int. Cl.
*A61N 1/39* (2006.01)

(52) U.S. Cl. .............................. 607/5; 607/36

(58) Field of Classification Search ........... 600/5, 33–37
See application file for complete search history.

(56) References Cited

U.S. PATENT DOCUMENTS

| 3,904,861 | A | 9/1975 | McNamara |
| 4,101,787 | A | 7/1978 | Vail |
| 4,590,943 | A | 5/1986 | Paull et al. |
| 5,224,870 | A | 7/1993 | Weaver et al. |
| 5,314,451 | A | 5/1994 | Mulier |
| 5,350,317 | A | 9/1994 | Weaver et al. |
| 5,372,605 | A | 12/1994 | Adams et al. |
| 5,470,343 | A | 11/1995 | Fincke et al. |
| 5,483,165 | A | 1/1996 | Cameron et al. |
| 5,562,710 | A | 10/1996 | Olsen et al. |
| 5,579,234 | A | 11/1996 | Wiley et al. |
| 5,591,213 | A | 1/1997 | Morgan et al. |
| 5,593,426 | A | 1/1997 | Morgan et al. |
| 5,640,078 | A | 6/1997 | Kou et al. |
| 5,645,571 | A | 7/1997 | Olson et al. |
| 5,658,316 | A | 8/1997 | Lamond et al. |
| 5,697,955 | A | 12/1997 | Stolte |
| 5,700,281 | A | 12/1997 | Brewer et al. |
| 5,721,482 | A | 2/1998 | Benvegar et al. |
| 5,741,305 | A | 4/1998 | Vincent et al. |
| 5,749,902 | A | 5/1998 | Olson et al. |
| 5,773,961 | A | 6/1998 | Cameron et al. |
| 5,782,878 | A | 7/1998 | Morgan et al. |

(Continued)

OTHER PUBLICATIONS

Heartstream.RTM., Fore Runner.RTM. Semi-Automatic Defibrillator User's Guide, pp. 6-9 and 50, no date.

(Continued)

*Primary Examiner* — Brian T Gedeon
(74) *Attorney, Agent, or Firm* — King & Spalding LLC

(57) ABSTRACT

The connector between the patient electrode pads and the base unit of an automatic external defibrillator (AED) system can be formed by capturing a printed circuit board (PCB) within a connector housing. The PCB can have conductive metal traces that serve as the contact points between the wires from the patient electrodes and the electronics within the AED base unit. The PCB in combination with the conductive metal traces can be shaped similar to a conventional two-prong or two-blade connector. Employing such a PCB-based connector may result in AED pads which are less complex and less costly to manufacture. The PCB can also support a configuration circuit that is positioned between the conductive metal traces and that allows the AED to read and store information about the attached pads. For example, the AED can use this data storage feature to check the expiration date of the pads.

11 Claims, 10 Drawing Sheets

U.S. PATENT DOCUMENTS

| | | |
|---|---|---|
| 5,791,907 A | 8/1998 | Ramshaw et al. |
| 5,792,190 A | 8/1998 | Olson et al. |
| 5,797,969 A | 8/1998 | Olson et al. |
| 5,800,460 A | 9/1998 | Powers et al. |
| 5,817,151 A | 10/1998 | Olson et al. |
| D405,754 S | 2/1999 | Barkley et al. |
| 5,868,790 A | 2/1999 | Vincent et al. |
| 5,868,794 A | 2/1999 | Barkley et al. |
| 5,879,374 A | 3/1999 | Powers et al. |
| 5,889,388 A | 3/1999 | Cameron et al. |
| 5,897,576 A | 4/1999 | Olson et al. |
| D409,752 S | 5/1999 | Bishay et al. |
| 5,904,707 A | 5/1999 | Ochs et al. |
| 5,913,685 A | 6/1999 | Hutchins |
| 5,919,212 A | 7/1999 | Olson et al. |
| 5,929,601 A | 7/1999 | Kaib et al. |
| 5,944,741 A | 8/1999 | Ochs et al. |
| 5,955,956 A | 9/1999 | Stendahl et al. |
| 5,964,786 A | 10/1999 | Ochs et al. |
| 5,983,137 A | 11/1999 | Yerkovich |
| 5,999,493 A | 12/1999 | Olson |
| 6,016,059 A | 1/2000 | Morgan |
| 6,021,352 A | 2/2000 | Christopherson et al. |
| 6,038,473 A | 3/2000 | Olson et al. |
| 6,075,345 A | 6/2000 | Lee |
| 6,101,413 A | 8/2000 | Olson et al. |
| 6,141,584 A | 10/2000 | Rockwell et al. |
| 6,148,233 A | 11/2000 | Owen et al. |
| 6,152,754 A | 11/2000 | Gerhardt et al. |
| 6,169,387 B1 | 1/2001 | Kaib |
| 6,201,992 B1 | 3/2001 | Freeman |
| 6,219,569 B1 | 4/2001 | Kelly et al. |
| 6,230,053 B1 | 5/2001 | Magin |
| 6,263,245 B1 | 7/2001 | Snell |
| 6,278,366 B1 | 8/2001 | Fletcher et al. |
| 6,301,502 B1 | 10/2001 | Owen et al. |
| 6,304,780 B1 | 10/2001 | Owen et al. |
| 6,314,320 B1 | 11/2001 | Powers et al. |
| 6,334,070 B1 | 12/2001 | Nova et al. |
| 6,360,120 B1 | 3/2002 | Powers et al. |
| 6,363,282 B1 | 3/2002 | Nichols et al. |
| 6,366,809 B1 | 4/2002 | Olson et al. |
| 6,370,428 B1 | 4/2002 | Snyder et al. |
| 6,374,137 B1 | 4/2002 | Morgan et al. |
| 6,374,138 B1 | 4/2002 | Owen et al. |
| 6,381,492 B1 | 4/2002 | Rockwell et al. |
| 6,386,882 B1 | 5/2002 | Linberg |
| 6,397,104 B1 | 5/2002 | Miller et al. |
| 6,405,083 B1 | 6/2002 | Rockwell et al. |
| 6,418,342 B1 | 7/2002 | Owen et al. |
| 6,427,083 B1 | 7/2002 | Owen et al. |
| 6,438,417 B1 | 8/2002 | Rockwell et al. |
| 6,442,433 B1 | 8/2002 | Linberg |
| 6,480,745 B2 | 11/2002 | Nelson et al. |
| 6,497,655 B1 | 12/2002 | Linberg et al. |
| 6,546,285 B1 | 4/2003 | Owen et al. |
| 6,586,850 B1 | 7/2003 | Powers |
| 6,597,948 B1 | 7/2003 | Rockwell et al. |
| 6,623,312 B2 | 9/2003 | Merry et al. |
| 6,648,823 B2 | 11/2003 | Thompson |
| 6,650,942 B2 | 11/2003 | Howard et al. |
| 6,671,545 B2 | 12/2003 | Fincke |
| 6,681,899 B1 | 1/2004 | Hong |
| 6,697,671 B1 | 2/2004 | Nova et al. |
| 6,721,602 B2 | 4/2004 | Engmark et al. |
| 6,754,538 B2 | 6/2004 | Linberg |
| 6,799,072 B2 | 9/2004 | Ries et al. |
| 6,820,998 B2 | 11/2004 | Chen |
| 6,878,112 B2 | 4/2005 | Linberg et al. |
| 6,920,360 B2 | 7/2005 | Lee et al. |
| 6,944,498 B2 | 9/2005 | Owen et al. |
| 6,955,864 B1 | 10/2005 | Vaisnys et al. |
| 6,978,182 B2 | 12/2005 | Mazar et al. |
| 6,990,371 B2 | 1/2006 | Powers et al. |
| 6,993,386 B2 | 1/2006 | Lin et al. |
| 7,165,998 B2 | 1/2007 | Lee et al. |
| 2002/0019170 A1 | 2/2002 | Hassanzadeh et al. |
| 2002/0026224 A1 | 2/2002 | Thompson et al. |
| 2002/0032470 A1 | 3/2002 | Linberg |
| 2002/0082644 A1 | 6/2002 | Picardo et al. |
| 2002/0095196 A1 | 7/2002 | Linberg |
| 2003/0004547 A1 | 1/2003 | Owen et al. |
| 2003/0050539 A1 | 3/2003 | Naghavi et al. |
| 2003/0055460 A1 | 3/2003 | Owen et al. |
| 2003/0068914 A1 | 4/2003 | Merry et al. |
| 2003/0144711 A1 | 7/2003 | Pless et al. |
| 2003/0205988 A1 | 11/2003 | Vaisnys et al. |
| 2004/0059405 A1 | 3/2004 | White et al. |
| 2004/0122488 A1 | 6/2004 | Mazar et al. |
| 2004/0133244 A1 | 7/2004 | Vaisnys et al. |
| 2004/0143298 A1 | 7/2004 | Nova et al. |
| 2004/0215278 A1 | 10/2004 | Stegink et al. |
| 2005/0036294 A1 | 2/2005 | McMahon |
| 2005/0137653 A1 | 6/2005 | Friedman et al. |
| 2005/0159787 A1 | 7/2005 | Linberg et al. |
| 2005/0225983 A1 | 10/2005 | Fornell |
| 2005/0261742 A1 | 11/2005 | Nova et al. |

OTHER PUBLICATIONS

Hewlett Packard, 43110 A Defibrillator/Monitor Operating Guide, Eighth Edition, pp. 2, 5,, 36-39, Aug. 1991.

Agilent Heartstream FR2, M3860A, M3861A, User's Guide, pp. 2-1-2-2, 2-4, 4-5, and B6, 2000.

Medtronic Physio-Control, Lifepack.RTM. 500 automated external defibrillator, Service Manual, pp. 3 of 12-4-12, 7 of 12-10 of 12, 12 of 12, 2001.

Medtronic Physio-Control, Lifepak.RTM. 500 Automated External Defibrillator Operating Instructions, pp. 2-5-2-6, 5-7-5-11, 5-16-5-17, Mar. 2001.

Survivalink FirstSave.TM. Operation and Service Manual, pp. 20, 29-31, 65, 70,84 and 85, 2000.

Swerdlow et al., "Cardiovascular Collapse Caused by Electrocardiographically Silent 60-Hz Intracardiac Leakage Current", 1999, American Heart Association, pp. 1-13.

International Search Report dated Sep. 14, 2007 for International Application No. PCTUS06/10423.

Office Action dated Oct. 22, 2008 for U.S. Appl. No. 11/386.051.

Office Action dated Jan. 29, 2009 for U.S. Appl. No. 11/386,051.

Office Action dated Nov. 24, 2009 for U.S. Appl. No. 11/386,051.

PCB BLADE CONNECTOR SYSTEM AND METHOD

CROSS REFERENCE TO RELATED APPLICATION

This application is a divisional of U.S. application Ser. No. 11/386,051, now U.S. Pat. No. 7,912,543, filed Mar. 21, 2006, entitled, "PCB Blade Connector System and Method", the entire contents of which are hereby incorporated by reference.

TECHNICAL FIELD

The present invention is generally directed to cardiac defibrillation technology, and relates more particularly to a connector for interfacing defibrillation pads to an automatic external defibrillator (AED) where the connector comprises a printed circuit board and optional configuration circuitry.

BACKGROUND OF THE INVENTION

Automatic external defibrillators (AEDS) are defibrillators that are designed to be operated by users with minimal training. Because AEDs can be used by non-medical personnel to treat sudden cardiac arrest (SCA), they are being deployed in a myriad of locations outside of traditional medical settings. As a result, more and more non-medical establishments are purchasing AEDs for deployment in their environments. Because of this ease of use, reliability and cost have become important factors in the design of AED devices.

An AED generally comprises a base unit and a defibrillation pad assembly. The defibrillation pad assembly generally comprises patient electrodes, a connector assembly, and wires interconnecting the patient electrodes and the connector assembly. The patient electrodes are also known as defibrillation pads. These electrodes are attached to the patient and serve to interconnect, via the wires and connector assembly, the patient to the AED. This interconnection enables both receiving electrocardiogram (ECG) signals from the patient and delivering defibrillation shocks to the patient. Defibrillation pad assemblies for AED systems are generally single-use, disposable items. As the applications of AED systems in non-medical environments increase, the need becomes more significant to reduce cost and facilitate ease-of-use.

As the connector assembly can be a significant cost component of the defibrillator pad assembly, it is desirable to reduce the cost of manufacturing the connector assembly. Generally, metal pin or metal blade style contacts within the connector assembly serve as the interconnection sites between the AED base and defibrillation pad assembly. Coupling these metal pin or blade contacts to the electrode wires and forming the contacts within the connector housing generally requires considerable handling during manufacture and may also require special tooling. This equipment and labor increases the cost of the connector assemblies for AED systems.

In general, the base unit of an AED system has no information as to the nature of the defibrillation pad assembly connected to it. Generally, defibrillation pad assemblies have a human readable expiration date and are only intended to be used once. Typically, an AED base unit cannot determine the age or history of a connected pad assembly. Thus an operator may attempt to operate the AED with a used or expired pad assembly without warning.

Used or expired defibrillation pads may be less conductive which may result in less effective rescue attempts. Likewise, an AED base unit that cannot determine what type of pad assembly is attached, is usually unable to adjust the level of shock energy supplied to the pad assembly. For example, a defibrillation pad assembly may be intended for a specific use such as adults, children, or training. If the AED could not sense that child pads were connected, it could not automatically adjust the shock energy to a lower level that could be helpful for child patients. Improperly adjusted shock energy levels may result in less effective rescue attempts.

In light of the manufacturing complexity and tooling requirements of metal pin or blade style contacts, there is a need for a connector system that may reduce the cost and manufacturing complexity of the connector assembly thereby reducing the cost of the defibrillation pad assembly. Since an AED that determines the history, expiration date, and intended use for an attached pad assembly may assure more effective rescue attempts, there is a need for configuration information to be stored within a connector system which the AED base unit may read from and write to. Given the minimal training requirements for the operators of AED systems, automatic and intelligent functionality within the AED unit is highly desirably.

SUMMARY OF THE INVENTION

An inventive connector system can comprise a mechanical structure that includes a printed circuit board (PCB) that can be made into one or more predetermined shapes. According to one exemplary aspect, the connector system can have a unique geometry for establishing an electrical connection between defibrillation pads and an automatic external defibrillator (AED). According to another exemplary aspect, the inventive connector system can also comprise a configuration circuit that stores information about the defibrillation pads. The configuration circuit may be characterized as the "intelligence" of the inventive connector system. The configuration circuit can allow an AED to sense if defibrillator pads are present. The inventive connector system can reduce the cost of defibrillation pad assemblies thorough use of PCB technology and it can also simplify the use of AED systems.

The inventive connector system can also simplify the mass production of defibrillation pad assemblies with its use of PCB technology to form exposed conductive trace contact areas on a rigid substrate. These exposed conductive trace contact areas may serve as the connection points between the defibrillator pad and the AED. According to one exemplary aspect, the PCB in combination with one or more conductive trace contact areas may be shaped similar to a conventional two-prong or two-blade connector with a notch or cut-out portion that separates the two conductive trace contact areas present on one side or face of the PCB.

According to another exemplary aspect, two conductive trace contact areas are present on each side or planar face of the PCB. On each side or planar face of a PCB, a conductive contact trace is positioned on a respective "blade" of the two-blade geometry. PCB technology is well understood to one of ordinary skill in the art. With using predetermined geometries and well planned electronic packaging of PCB technology, the system can be manufactured quickly, at a low cost, without special tooling, and without a high degree of precision.

According to one exemplary aspect, with the inventive system having the unique geometry, the configuration circuit can be positioned adjacent to the notch and between two conductive trace contact areas on one side or planar face of the PCB. On an opposite side of the planar PCB, the other pair of conductive trace contact areas that are positioned on the blades can connect to the wires from the patient electrodes. The entire PCB can be contained in a connector housing. While some of the illustrated geometries are exemplary features of the invention, one of ordinary skill in the art recognizes that use of PCB technology permits the connector system to have many other different shapes not illustrated. That is, the invention is not limited to the PCB geometry shown in the drawings and it is apparent that other geometries of the PCB board with its conductive contact areas are within the scope of the invention.

Low-cost component-on-PCB technology allows the PCB to be populated on one side with the configuration circuit. The configuration circuit can comprise non-volatile memory with a one-wire interface. Control logic in the AED base unit can interface with this configuration circuit through additional contacts in the connector assembly.

The configuration circuit may store information such as the expiration date of the pad assembly, physical characteristics of the pad assembly, intended use of the pad assembly (e.g. training, adult, or child), and a record of the use of the pad assembly. Such configuration information related to the pad assembly may allow the control logic within the AED to make intelligent use of the pad assembly for purposes such as reducing the defibrillation energy when a child pad is in use, and notification of an out-of-date pad in use. Such information may allow an AED to warn its operator of potential improper use during self-tests and to generally interact with its environment more intelligently. The configuration circuit also allows an AED to sense the presence of defibrillation pads. These array of features and functions result in an AED system that is easier to use and less prone to misuse due to operator error. These improvements can be beneficial as AED systems are available in more non-medical environments.

DETAILED DESCRIPTION OF EXEMPLARY EMBODIMENTS

The inventive connector system may comprise a connector assembly disposed at the end of a set of wires which extend from a set of defibrillation pads. The inventive connector system can serve as the attachment mechanism between the defibrillation pads and an AED. One embodiment of the connector system may engage with a female connector on or within an AED base unit.

One embodiment of the connector system may comprise a printed circuit board (PCB) positioned within the connector assembly and partially exposed from a connector assembly housing. When the connector system is engaged with an AED base unit, one or more conductive traces on the exposed portion of the PCB can serve as the electrical contacts between the AED base unit and the defibrillation pad assembly.

According to another exemplary embodiment, the inventive connector system may comprise a configuration circuit that provides the "intelligence" of the connector system. The configuration circuit may be readable from the AED base unit. The configuration circuit may also be writable from the AED base unit. The configuration circuit may store, report, or record information such as: pad assembly serial number, pad assembly expiration date, intended pad use, and a history of prior use of the pad assembly. The configuration circuit may comprise a non-volatile, electrically-programmable memory device. The memory device may comprise a semiconductor memory populated on the aforementioned PCB. An alternative embodiment of the configuration circuit may comprise electrically fusible elements that are one-time writable.

Figure 1:
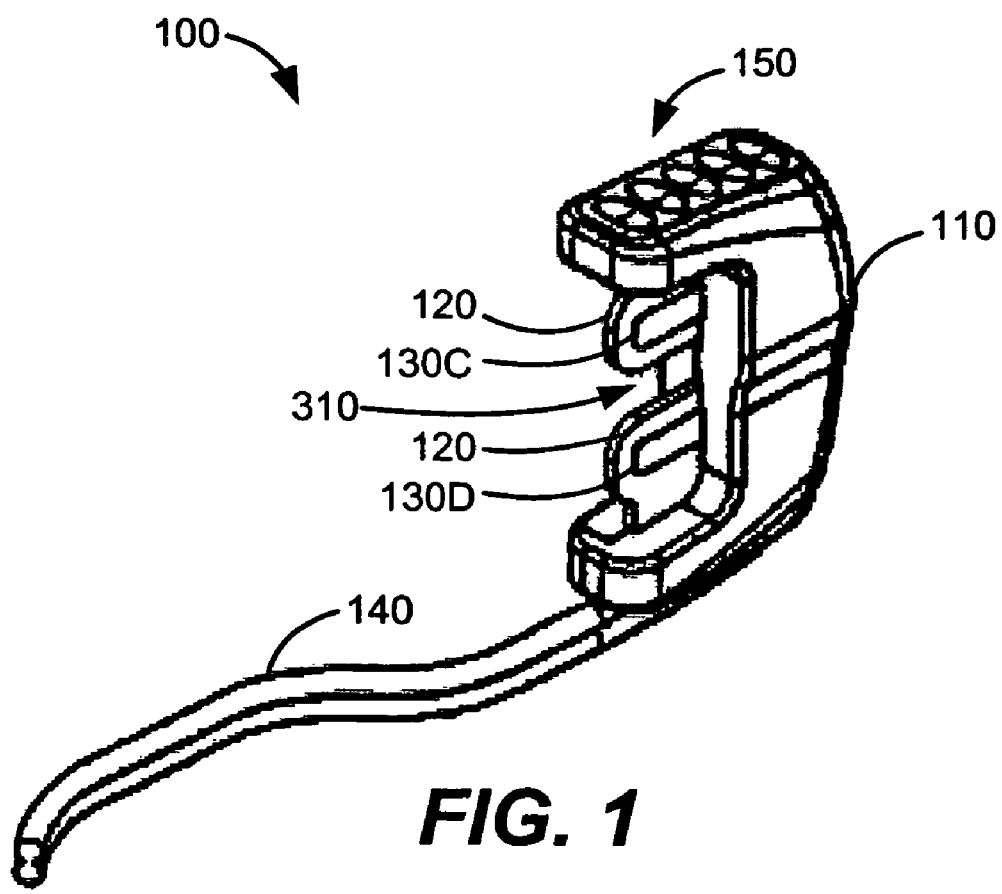
FIG. 1 illustrates a perspective view of a connector according to one exemplary embodiment of the invention.

Turning now to the drawings, in which like reference numerals refer to like elements, FIG. 1 illustrates a perspective view of connector assembly 100 according to one exemplary embodiment of the invention. PCB 120 comprises a rigid substrate and pairs of conductive trace contact areas 130. In FIG. 1, a first pair of contact areas 130C and 130D are visible while a second pair of contact areas 130A and 130B are on the opposite side of the PCB 120 and are not visible in this view. A more detailed illustration of an exemplary PCB 120 in FIG. 8 provides a view of both a first pair and a second pair of contact areas 130.

PCB 120 can be manufactured using a standard circuit board etching technique on copper clad fiber/resin substrate. PCB 120 is positioned within connector housing 110 such that conductive trace contact areas 130 are exposed for electrical mating with an AED base unit. The PCB 120 in combination with the four conductive trace contact areas 130A, 130B, 130C, and 130D may be shaped similar to a conventional two-prong or two-blade connector with a notch or cut-out portion 310 (See FIG. 3A) separating the conductive trace contact areas 130. While the first pair of conductive trace contact areas 130C and 130D are illustrated in FIG. 1, and the second pair of conductive trace contact areas 130A and 130B are hidden on the opposite planar side or face of PCB 120, it should be appreciated that additional contact areas 130 could be added with out departing from the scope and spirit of the invention.

Figure 2:
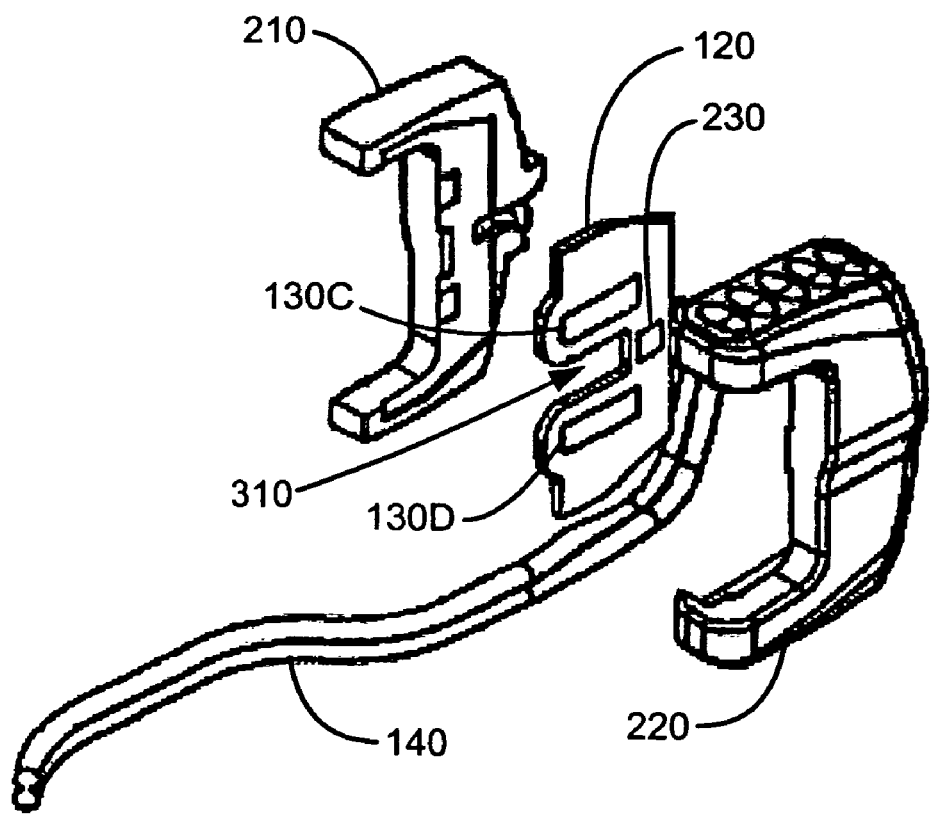
FIG. 2 is an exploded perspective view of the exemplary embodiment illustrated in FIG. 1.

Referring now to FIG. 2, a configuration circuit 230 can be positioned on the planar PCB 120 adjacent to the notch 310 and between the two conductive trace contact areas 130. A second pair of conductive trace contact areas 130A, 130B on a first planar side or face of the PCB 120 (not illustrated in FIG. 2, but illustrated in FIG. 8) are in electrical communication with wires 140 which connect to the patient electrodes. A first pair of conductive trace contact areas 130C, 130D on a second planar side or face of the PCB 120 illustrated in FIG. 2 are in electrical communication with the configuration circuit 230.

Connector housing 110 can be formed from two elements of molded plastic material which are fastened, glued, snapped together, or formed around PCB 120. The shape of housing 110 allows mating into an AED base unit and facilitates insertion and extraction through an optional molded gripping surface 150. One of ordinary skill in the art will appreciate that the plastic material of the connector housing 110, the fiber resin of PCB substrate 120 and the copper conductive traces 130 of the PCB 120 may each comprise numerous other materials or combinations without departing from the spirit and scope of the invention.

According to one preferred, yet exemplary embodiment, PCB 120 comprises a U-shaped rigid substrate in which each side of the "U" includes a first pair of conductive trace contact areas 130C and 130D. Again, the second pair of conductive trace contact areas 130A and 130B are on the opposite planar side of the PCB 120 and are not visible in FIG. 2 but are illustrated in FIG. 8. The notch 310 forms the central region of the U-shape. The notch 310 within this U-shaped PCB 120 can provide a benefit of maintaining conductive trace contact areas 130 physically separated.

Figure 6:
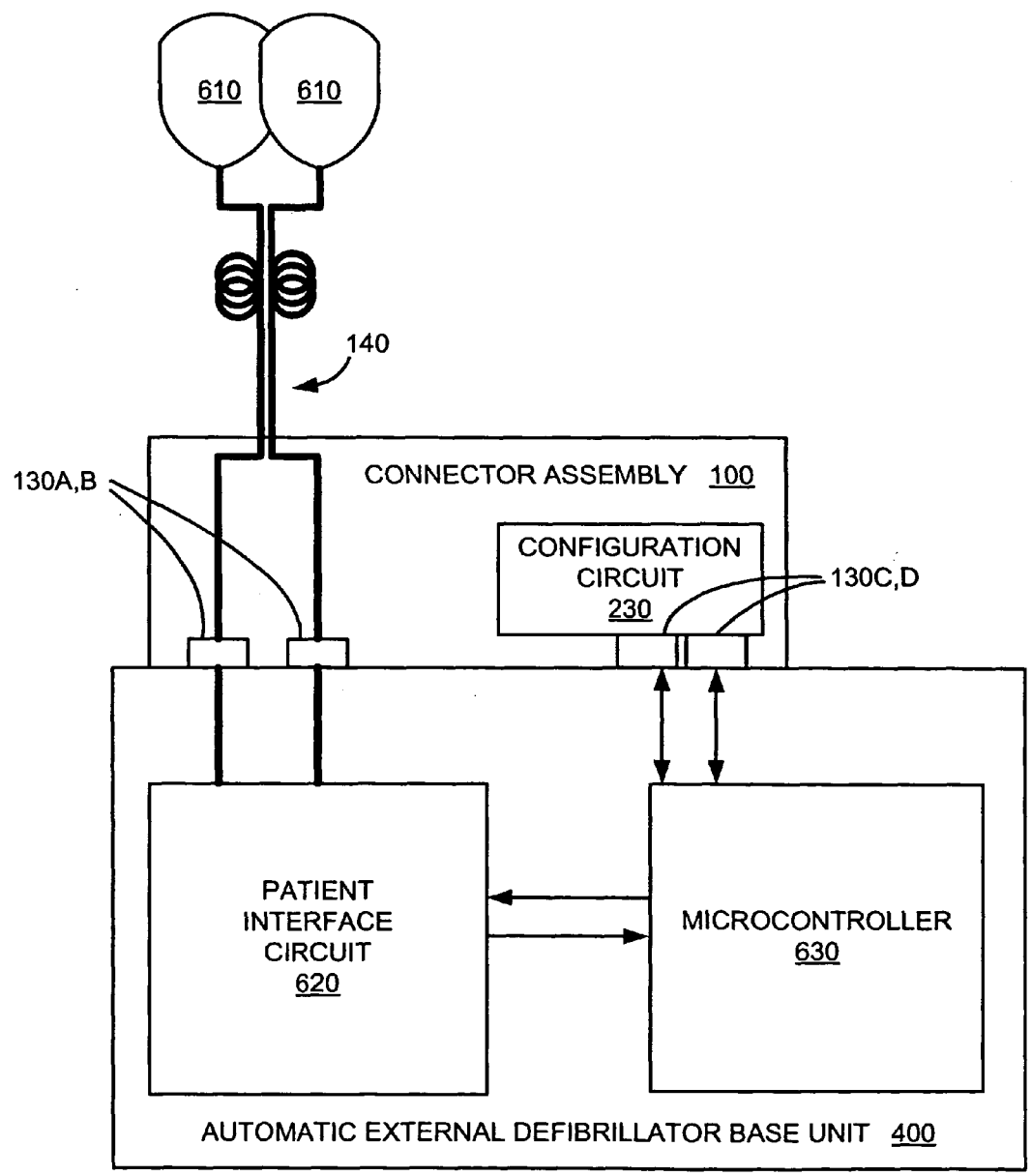
FIG. 6 is a functional block diagram illustrating the interconnections into and through a connector assembly according to one exemplary embodiment of the invention.

This physical separation can be advantageous when the second pair of contact areas 130A, 130B is used to support high voltage connections such as for electrodes 610 (illustrated in FIG. 6). However, it is apparent to one of ordinary skill in the art that other geometries of PCB 120 are not beyond the scope of the invention. Other PCB geometries not illustrated can be readily designed in order to optimize manufacturing steps. One way to optimize manufacturing steps may be to use geometries that can be mass produced and that do not require special tooling for manufacturing machinery.

Adjacent to the central region of the exemplary U-shape and on a planar side opposite to the first pair of electrodes 130A, 130B, configuration circuit 230 can be positioned on PCB 120, according to one exemplary embodiment. The configuration circuit 230 can be enclosed by first and second connector housing elements 210 and 220. In the illustrated exemplary embodiment, connector housing elements 210 and 220 can also have a U-shape and combine to form the connector housing 110. Housing element 210 can form inside housing element 220 such that the seams between them are not on outer gripping surface 150. A snap together embodiment of the housing may eliminate screws and hinges.

Figure 3A:
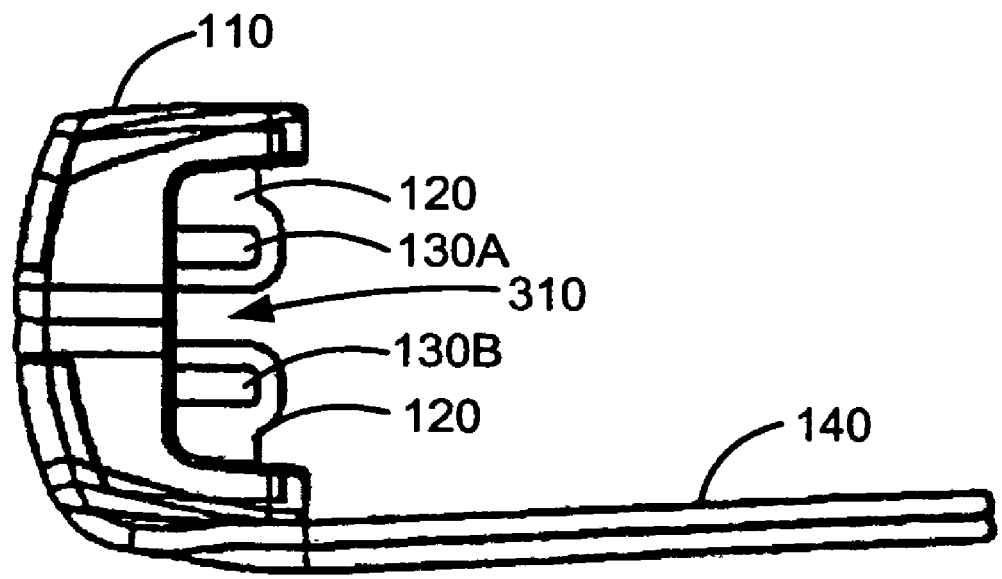
FIG. 3 are alternate views of the exemplary embodiment illustrated in FIGS. 1 and 2.

FIG. 3A illustrates a plan view of an exemplary embodiment of the invention where partially exposed PCB 120 is positioned within connector housing 110. The U-shape of connector housing 110 can provide a form-fit seating into the housing of the AED base unit 400. Form-fitting of the connector housing 110 into the AED base unit 400 may provide keying to prevent other connectors from being inserted and to ensure the correct polarity of insertion of the connector 100 into the AED base unit 400. The sides of the U-shaped housing 110 can serve as a gripping surface 150 and also provide insulation of the electrical contacts of enclosed PCB 120. PCB 120 comprises conductive trace contact areas 130 which are in electrical communication with wires 140. Notch 310 in PCB 120 provides mechanical keying during the mating of the connector and the AED base unit. This keying assists in orientation and alignment of the connector with respect to the AED base unit. Alternatively, notch 310 may comprise any insulating separation to electrically isolate the contact areas 130A and 130B. The unique shape or geometry of PCB 120 also prevents incorrect pad assemblies from being inserted into the AED base unit. In this figure, the configuration circuit 230 is not visible because it is enclosed by connector housing 110.

Figure 3B:
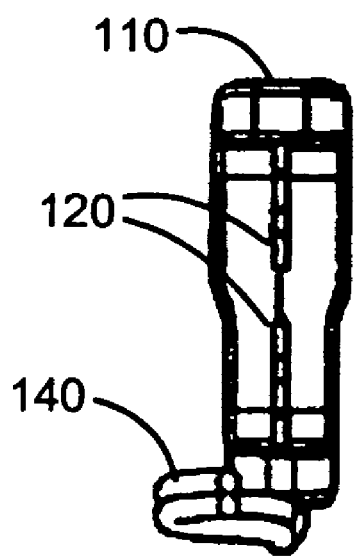

FIG. 3B illustrates an elevation view of an exemplary embodiment of the invention where patient electrode wires 140 extend from connector housing 110. Partially exposed PCB 120 is captured within connector housing 110.

Figure 4:
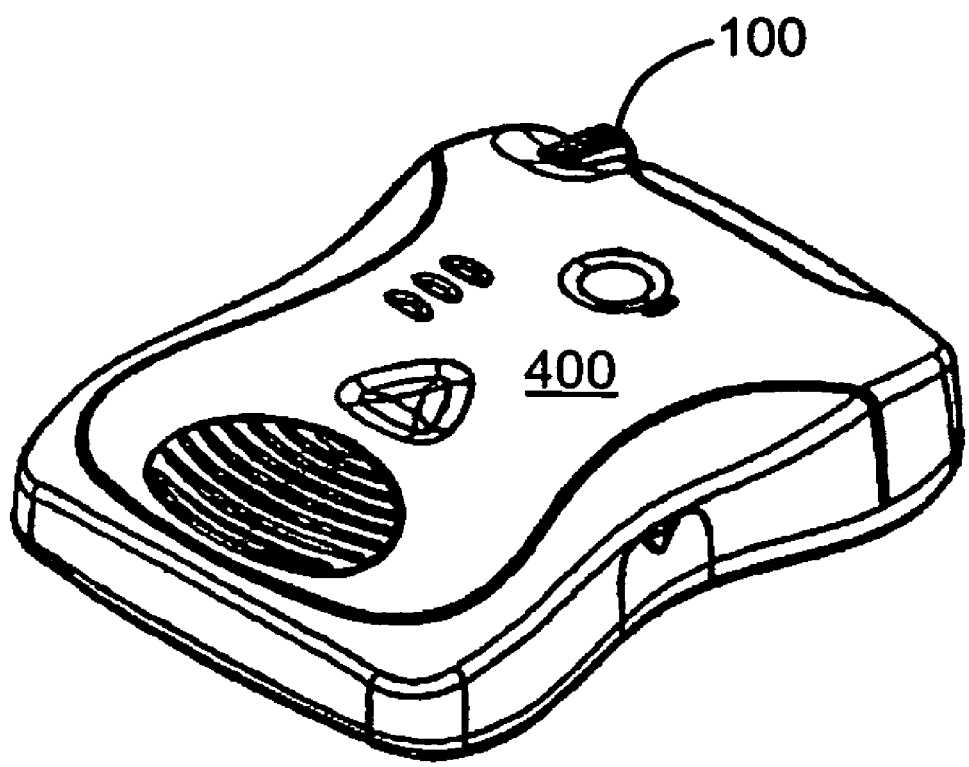
FIG. 4 is a perspective view of the exemplary embodiment illustrated in FIGS. 1-3 when engaged with an AED base unit according to one exemplary embodiment of the invention.

FIG. 4 illustrates a perspective view of one exemplary embodiment of the invention while engaged with an AED base unit. Connector assembly 100 can engage with an AED base unit 400. In this figure, patient electrode wires 140 are not illustrated.

Figure 5:
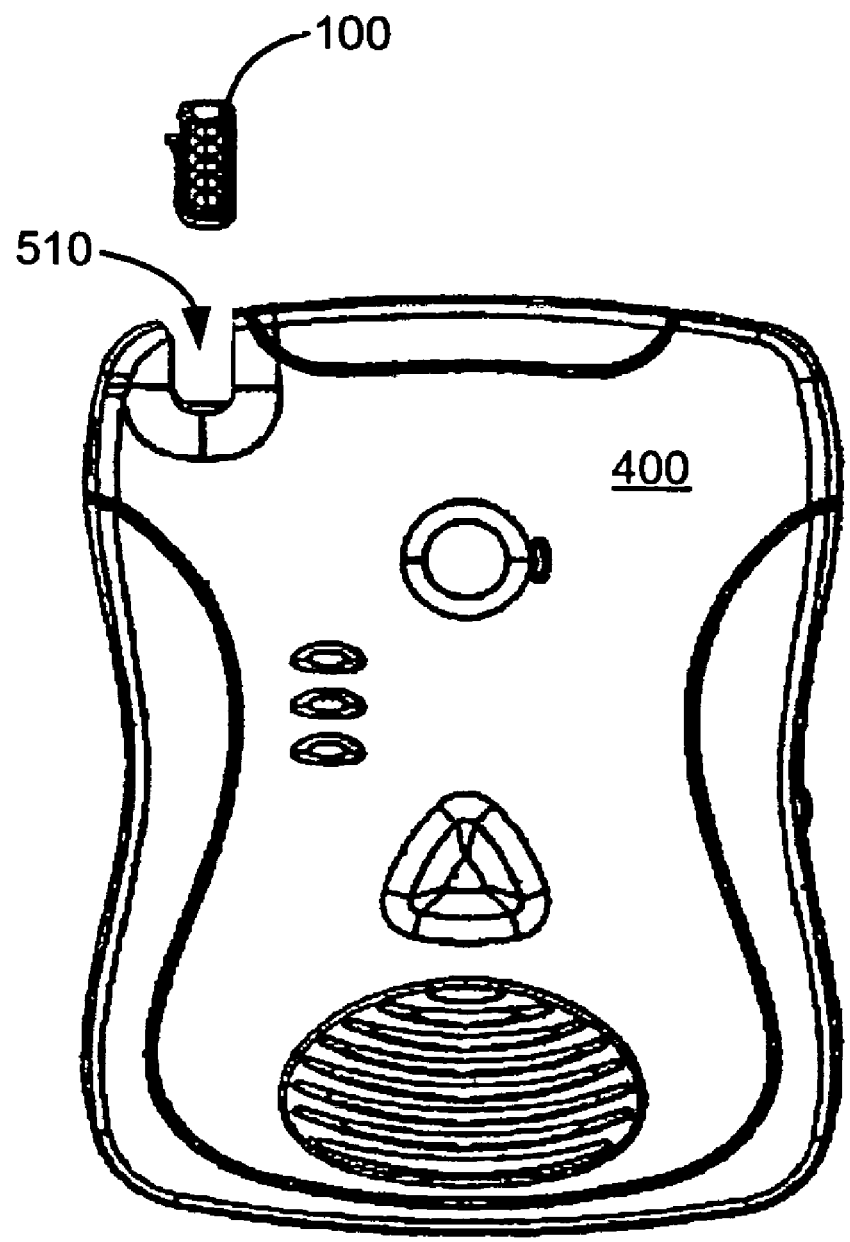
FIG. 5 illustrates an exemplary embodiment of the invention mating with an AED.

FIG. 5 illustrates an exemplary embodiment of the invention mating with an AED base unit. Connector assembly 100 inserts into AED base unit 400 at a notch 510.

FIG. 6 illustrates a functional block diagram according to one exemplary embodiment of the invention. Patient electrodes 610 are connected by wires 140 to conductive trace contacts 130A, 130B within connector assembly 100. Connector assembly 100 mates with AED base unit 400. Conductive trace contacts 130A, 130B within connector assembly 100 are the electrical communication interface between patient electrodes 610 and patient interface circuit 620 within AED base unit 400. Patient electrodes 610 are used to both receive ECG signals from the patient and to deliver defibrillation shocks to the patient. Conductive trace contacts 130C, 130D within connector assembly 100 are the electrical communication interface between configuration circuit 230 and the microcontroller 630 within AED base unit 400.

Patient interface circuit 620 provides the analog front-end to microcontroller 630 for performing the ECG and shock functions. Microcontroller 630 within AED base unit 400 is the main processor unit of the AED performing functions such as user interface, self tests, ECG analysis, and in some cases, controlling a level of patient shock. Micro controller 630 within AED base unit 400 also directly reads and/or writes information stored in configuration circuit 230 through conductive trace contacts 130C, 130D. Configuration circuit 230 can be located within connector assembly 100 and stores information specific to each defibrillator pad assembly.

One of ordinary skill in the art will appreciate that configuration circuit 230 may comprise a non-volatile semiconductor memory device, fusible elements, jumpers, or numerous other forms without departing from the spirit and scope of the invention. One of ordinary skill in the art will also appreciate that microcontroller 630 may comprise a microcontroller, microprocessor, DSP processor, application specific logic, programmable logic, or numerous other forms without departing from the spirit and scope of the invention.

Figure 7:
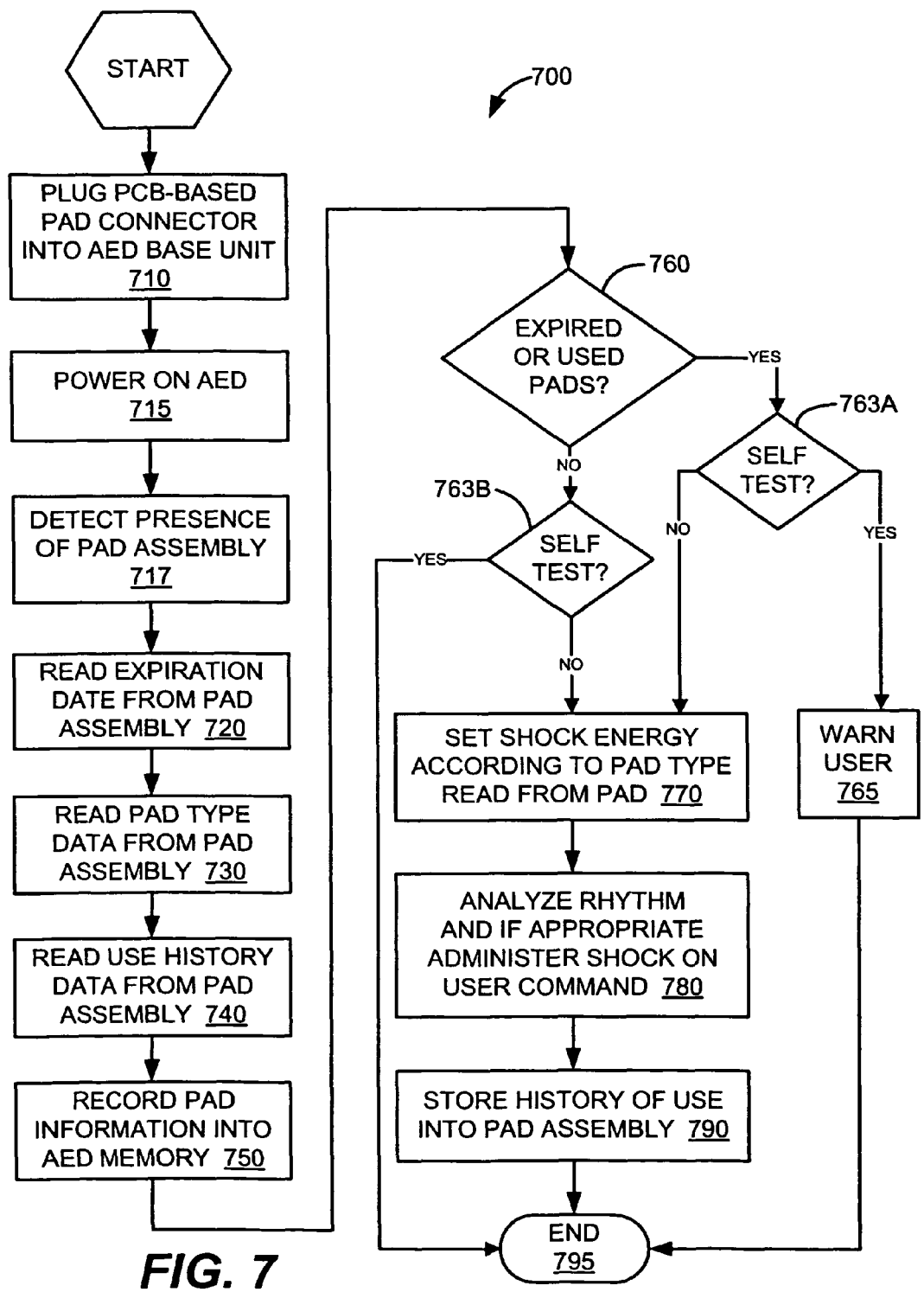
FIG. 7 is a logic flow diagram highlighting exemplary steps for use of a defibrillation pad configuration circuit by the microcontroller within an AED base unit according to one exemplary embodiment of the invention.

FIG. 7 illustrates a logical flow diagram 700 for a method of using configuration information retrieved from a configuration circuit by an AED. The logical flow diagram 700 highlights some key functional features of the combination of configuration circuit 230 and microcontroller 630. One of ordinary skill in the art will appreciate that process functions of microcontroller 630 may comprise firmware code executing on a microcontroller, microprocessor, or DSP processor; state machines implemented in application specific or programmable logic; or numerous other forms without departing from the spirit and scope of the invention. In other words, the invention may be provided as a computer program which may include a machine-readable medium having stored thereon instructions which may be used to program a computer (or other electronic devices) to perform a process according to the invention.

The machine-readable medium may include, but is not limited to, floppy diskettes, optical disks, CD-ROMs, magneto-optical disks, ROMs, RAMs, EPROMs, EEPROMs, magnet or optical cards, flash memory, or other type of media/machine-readable medium suitable for storing electronic instructions.

Certain steps in the processes or process flow described in all of the logic flow diagrams referred to below must naturally precede others for the invention to function as described. However, the invention is not limited to the order or number of the steps described if such order/sequence or number does not alter the functionality of the present invention. That is, it is recognized that some steps may be performed before, after, or in parallel to other steps without departing from the scope and spirit of the present invention. It is also recognized that additional or fewer steps may be performed without departing from the scope and spirit of the invention.

Further, one of ordinary skill in programming would be able to write such a computer program or identify the appropriate hardware circuits to implement the disclosed invention without difficulty based on the flow charts and associated description in the application text, for example. Therefore, disclosure of a particular set of program code instructions or detailed hardware devices is not considered necessary for an adequate understanding of how to make and use the invention. The inventive functionality of the claimed computer implemented processes will be explained in more detail in the following description in conjunction with the remaining Figures illustrating other process flows.

Step 710 is the first step in inventive connection and information retrieval process 700. Step 710 is a mechanical step in which connector assembly 100 is inserted into base unit 400 at notch 510. Notch 310 in PCB 120 provides mechanical keying during the mating of the connector system 100 and the AED base unit 400. In step 715, the AED is powered on. Next in step 717, the microcontroller 630 can detect the presence of the electrode pads 610 by sensing and communicating with the configuration circuit 230. If the microcontroller does not detect the presence of the electrode pads 610, the microcontroller 630 can alert the AED operator of this status.

In step 720, microcontroller 630 reads the expiration date of the pad assembly from configuration circuit 230. Next, in step 730, microcontroller 630 reads the information about the type of pad assembly from configuration circuit 230. Next, in step 740, microcontroller 630 reads the use history of the pad assembly from configuration circuit 230. Together, steps 720, 730 and 740 provide the AED base unit 400 with information about the pad assembly which is attached to it. In other embodiments, this information could include pad assembly serial numbers, manufacturing information, self test information, and various physical or electrical characteristics of the pads 610 or pad assembly. Microcontroller 630 may read any combination of one or more information elements in these steps. Therefore, anyone or more of Steps 720, 730, 740 may not be performed by the microcontroller 630 without departing from the scope of the invention.

In step 750, microcontroller 630 may record the information gathered from the pad assembly into the memory of the AED base unit 400 or an attached memory device. This record of attached pad assemblies may be used in the future to analyze the history of an AED system.

In decision step 760, microcontroller 630 uses configuration information read from the configuration circuit 230 in steps 720 and 740 to determine if the attached defibrillator pad assembly is used or past its expiration date. If the pad assembly is used or expired, meaning that the inquiry to decision step 760 is positive, then the process follows the "Yes" branch and the process continues to decision step 763A. If the inquiry to decision step 760 is negative, then the "No" branch is followed to decision step 763B.

In decision step 763A, the microcontroller 630 determines if a self test is being conducted. The purpose of decision step 763A is that the system will usually only warn a user about expired pads during a non-rescue mode. During a rescue mode in which the AED 400 may be used to save a patient, a warning about used or expired pads 610 could be distracting to the operator of the AED 400.

If the inquiry to decision step 763A is positive meaning that a self test is being conducted, then the process continues to step 765 in which microcontroller 630 may provide the operator with information regarding the status of the pad assembly in warning step 765. If the inquiry to decision step 763A is negative, then the "No" branch is followed to step 770.

Similar to decision step 763A, in decision step 763B, the microcontroller 630 determines if a self test is being conducted. If the inquiry to decision step 763B is positive meaning that a self test is being conducted, then the process continues to step 795 which is the end of the process. If the inquiry to decision step 763B is negative, then the "No" branch is followed to step 770.

In step 770, microcontroller 630 can use configuration information read in step 730 to set the defibrillation shock energy according to the intended use of the attached pad assembly. For example, a lower amount of shock energy would be delivered to pads 610 if the attached pads were for use on children, or the shock may be only simulated if the attached pads 610 were for use in operator training. However, it is recognized that the intended use of an attached pad assembly can be controlled by attenuators external to the AED 400 and that are part of the pad assembly. In such situations where pads 610 are under external attenuation control, step 770 can be skipped entirely or not performed by the microcontroller 630.

In step 780, the AED 400 performs the defibrillation steps of analyzing the patient's heart rhythm to determine if shocking is appropriate, informing the operator, awaiting operator approval, and finally providing the defibrillation shock.

In step 790, a shock event may be recorded into the pad assembly. Data in step 790 is stored into the configuration circuit 230 within the pad assembly to indicate use of the defibrillation pads 610 and may be read by microcontroller 630 during future operation of AED 400 to prevent reuse of the pad assembly comprising pads 610.

Figure 8A:
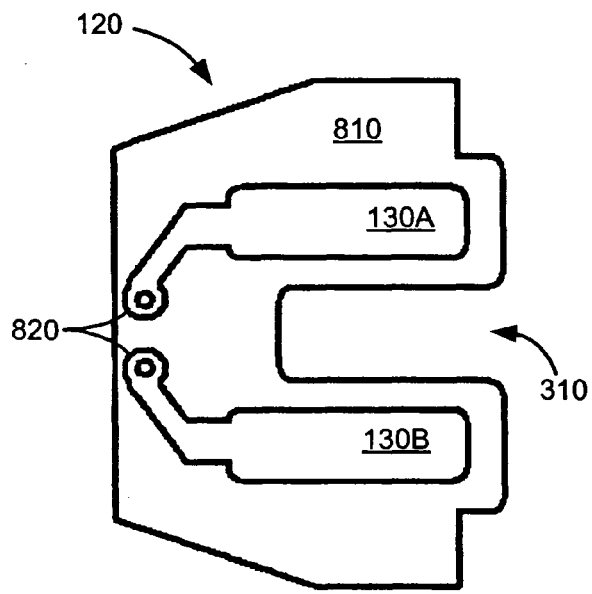
FIG. 8A and FIG. 8B illustrate plan views of a printed circuit board according to one exemplary embodiment of the invention.

FIG. 8A illustrates a plan view of PCB 120 according to an exemplary embodiment of the invention. PCB 120 comprises a rigid substrate 810 with notch 310 and the second pair of conductive trace contact areas 130A and 130B. The second pair of contact areas 130A and 130B are in electrical communication with connection areas 820 where patient electrode wires 140 (not illustrated in FIG. 8) may be attached to the PCB 120. The connection areas 820 can comprise through-hole vias for soldering wires 140, contact pads for surface soldering or compression contact of wires 140, or similar contacting mechanisms for attaching wires 140. The notch 310 within the U-shaped PCB 120 can provide a benefit of maintaining conductive trace the second pair of contact areas 130A, 130B physically separated. This physical separation between the second pair of contact areas can be advantageous because the second pair of contact areas 130A, 130B can support high voltage connections such as for electrodes 610. While some of the unique geometry, such as the notch 310 in PCB 120, illustrates exemplary features of the invention, one of ordinary skill in the art will recognize that using PCB technology can allow inventive the connector system to use many other different shapes not illustrated. The invention is not limited to the PCB geometry shown and it is apparent that other geometries are within the scope of the invention.

Figure 8B:
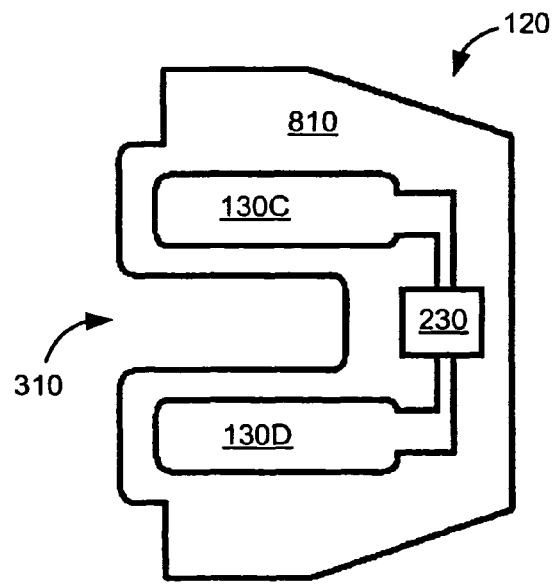

FIG. 8B illustrates a plan view of PCB 120 according to another exemplary embodiment of the invention. The view in FIG. 8B is the opposite side of the PCB 120 as illustrated in FIG. 8A. PCB 120 comprises a rigid substrate 810 with notch 310 and the first pair of conductive trace contact areas 130C and 130D. The first pair of contact areas 130C and 130D are in electrical communication with configuration circuit 230 to allow microcontroller 630 (not illustrated in FIG. 8) to communicate with configuration circuit 230.

The geometry and electronic packaging formed by the PCB technology illustrated in FIG. 8 for the inventive connector system can simplify the mass production of defibrillation pad assemblies. The PCB 120 in combination with the one or more conductive trace contact areas 130A-D may be shaped similar to a conventional two-prong or two-blade connector with a notch or cut-out portion 310 that separates the two pairs of conductive trace contact areas 130A-D present on each side or face of the PCB 120. With the unique geometry and electronic packaging of the inventive connector system 100, the system 100 can be manufactured quickly, at a low cost, without special tooling, and without a high degree of precision.

Figure 9:
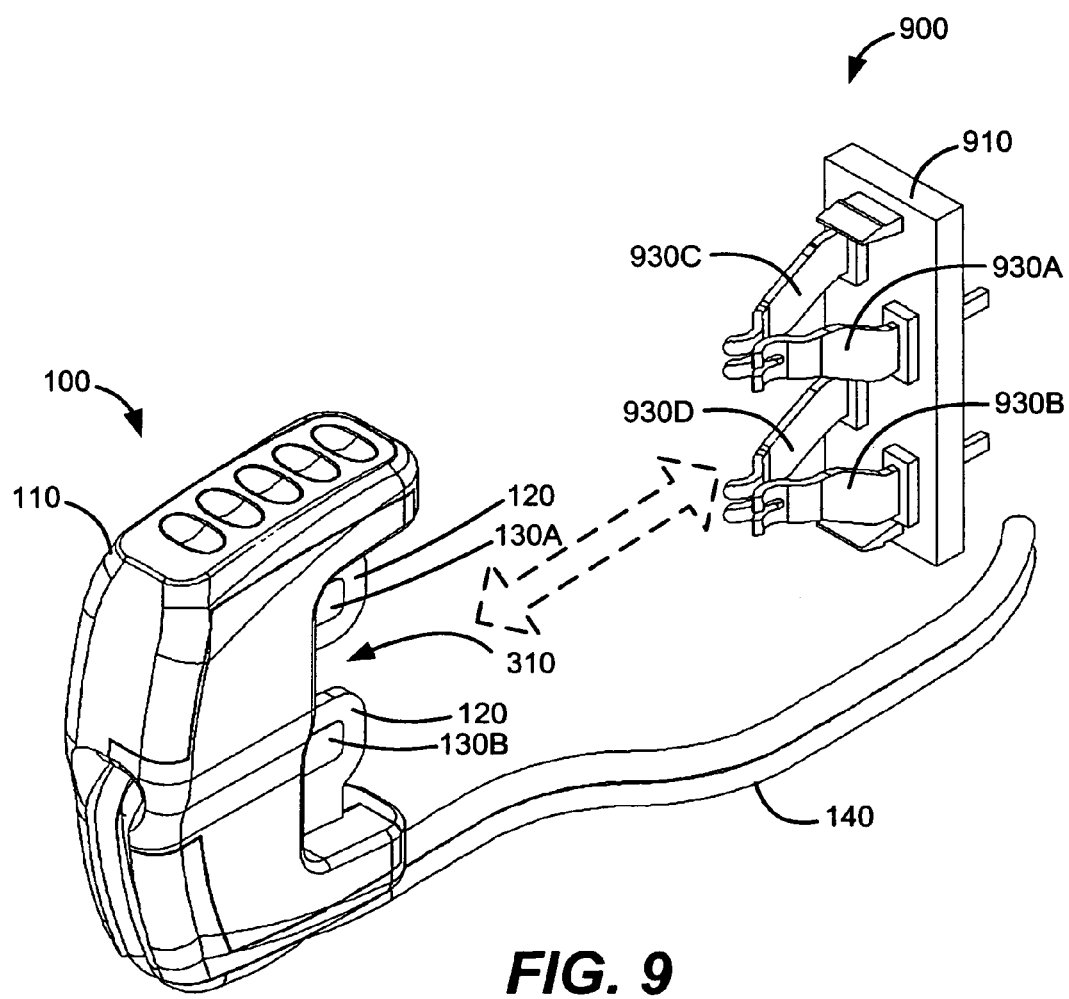
FIG. 9 illustrates a perspective view of a connector and the corresponding mating assembly according to one exemplary embodiment of the invention.

FIG. 9 illustrates a perspective view of a connector 100 and the corresponding mating assembly 900 according to one exemplary embodiment of the invention. When connector 100 is assembled, PCB 120 is formed inside of connector housing 110 such that first and second pairs of contact areas 130 are exposed beyond the housing 110 and so that they may mate with electrical contacts of assembly 900 which is inside AED 400 at notch 310. The second pair of conductive trace contact areas 130A and 130B are in electrical communication with wires 140 which connect to the patient electrodes. Stamped metal contacts 930 are anchored into brace 910 which is disposed inside AED 400 at notch 310.

Figure 10:
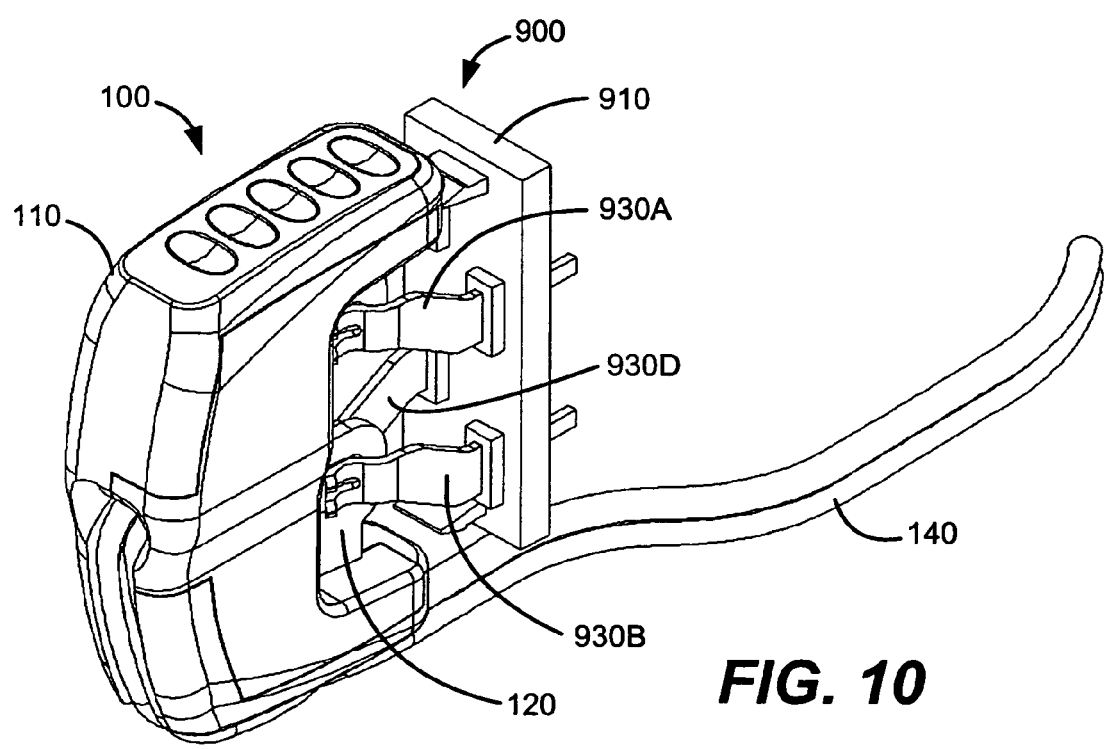
FIG. 10 illustrates a perspective view of a connector engaged with the corresponding mating assembly according to one exemplary embodiment of the invention.

Referring now to FIG. 10, this Figure illustrates the same perspective view of the connector 100 and the corresponding mating assembly 900 when they are engaged with one another. Once connector 100 and mating assembly 900 are engaged, stamped metal contact 930A is in electrical communication with contact trace 130A. Similarly, stamped metal contact 930B is in electrical communication with contact trace 130B, stamped metal contact 930C is in electrical communication with contact trace 130C, and stamped metal contact 930D is in electrical communication with contact trace 130D.

Alternative embodiments of the connector system will become apparent to one of ordinary skill in the art to which the present invention pertains without departing from its spirit and scope. Thus, although this invention has been described in exemplary form with a certain degree of particularity, it should be understood that the present disclosure has been made only by way of example and that numerous changes in the details of construction and the combination and arrangement of parts or steps may be resorted to without departing from the spirit or scope of the invention. Accordingly, the scope of the present invention is defined by the appended claims rather than the foregoing description.

What is claimed is:

1. A method for tracking and monitoring information about an electrode coupled to a defibrillator comprising:
    coupling the electrode to the defibrillator with a connector system, the connector system comprising a housing and two or more contacts, each contact comprising a conductive planar trace positioned on a printed circuit board for removably coupling to the defibrillator and for coupling the electrode to the defibrillator;
    reading information about the electrode with the defibrillator from a configuration circuit; and
    sending shock energy to the electrode if it is determined that one or more predetermined conditions are met.

2. The method of claim 1, further comprising sending information from the defibrillator to the configuration circuit.

3. The method of claim 1, further comprising storing the information received from the defibrillator in the configuration circuit.

4. The method of claim 1, wherein reading information about the electrode with the defibrillator from the configuration circuit comprises reading an expiration date.

5. The method of claim 1, further comprising determining if the electrode has expired.

6. The method of claim 1, further comprising reading a usage history of the electrode.

7. The method of claim 1, further comprising determining if the electrode has not been used.

8. The method of claim 1, wherein reading information with the defibrillator from a configuration circuit comprises the step of reading a defibrillator pad type.

9. The method of claim 1, further comprising adjusting a level of defibrillation shock energy based on information read from the configuration circuit.

10. The method of claim 1, further comprising determining if a self test is being executed and if information read from the configuration circuit indicates the electrode is one of expired and used.

11. The method of claim 3, wherein storing the information received from the defibrillator in the configuration circuit comprises storing a record of usage history for the electrode.

\* \* \* \* \*